(12) United States Patent
Schadendorf et al.

(10) Patent No.: US 9,861,688 B2
(45) Date of Patent: Jan. 9, 2018

(54) T CELL RECEPTORS WITH MHC INDEPENDENT BINDING TO GM-CSF RECEPTOR ALPHA CHAIN

(71) Applicants: Universitaetsmedizin der Johannes Gutenberg-Universitaet Mainz, Mainz (DE); Universitaet Duisberg-Essen, Essen (DE)

(72) Inventors: Dirk Schadendorf, Essen (DE); Annette Paschen, Essen (DE); Silke Luebcke, Mainz (DE); Martina Fatho, Woerrstadt (DE); Daniela Eberts, Finthen (DE); Hakim Echchannaoui, Mainz (DE); Volker Lennerz, Ober-Olm (DE); Catherine Woelfel, Mainz (DE); Thomas Woelfel, Mainz (DE)

(73) Assignees: Universitaetsmedizin der Johannes Gutenberg-Universitaet Mainz, Mainz (DE); Universitaet Duisburg-Essen, Essen (DE)

( * ) Notice: Subject to any disclaimer, the term of this patent is extended or adjusted under 35 U.S.C. 154(b) by 0 days.

(21) Appl. No.: 14/648,703

(22) PCT Filed: Dec. 16, 2013

(86) PCT No.: PCT/EP2013/076760
§ 371 (c)(1),
(2) Date: May 30, 2015

(87) PCT Pub. No.: WO2014/091034
PCT Pub. Date: Jun. 19, 2014

(65) Prior Publication Data
US 2015/0313978 A1 Nov. 5, 2015

(30) Foreign Application Priority Data
Dec. 14, 2012 (EP) .................................. 12197289

(51) Int. Cl.
| | | |
|---|---|---|
| A61K 6/00 | (2006.01) | |
| A61K 35/00 | (2006.01) | |
| A61K 35/12 | (2015.01) | |
| A61K 35/14 | (2015.01) | |
| A61K 35/17 | (2015.01) | |
| A61K 38/00 | (2006.01) | |
| A61K 39/00 | (2006.01) | |
| C07K 14/725 | (2006.01) | |
| C07K 14/715 | (2006.01) | |
| C12N 9/90 | (2006.01) | |
| G01N 33/569 | (2006.01) | |
| G01N 33/50 | (2006.01) | |

(52) U.S. Cl.
CPC .......... A61K 39/0011 (2013.01); A61K 35/17 (2013.01); C07K 14/7051 (2013.01); C07K 14/7153 (2013.01); C12N 9/90 (2013.01); G01N 33/5047 (2013.01); G01N 33/56972 (2013.01); A61K 38/00 (2013.01); A61K 2039/572 (2013.01); A61K 2039/585 (2013.01); C12Y 503/03012 (2013.01)

(58) Field of Classification Search
None
See application file for complete search history.

(56) References Cited

FOREIGN PATENT DOCUMENTS

| WO | WO 91/02063 | 2/1991 |
|---|---|---|
| WO | 9729195 A2 | 8/1997 |
| WO | 0248370 A2 | 6/2002 |
| WO | WO 2007/110631 A1 | 10/2007 |
| WO | WO 2007/131092 A2 | 11/2007 |
| WO | 2008039818 A2 | 4/2008 |
| WO | WO 2008/039818 A2 * | 4/2008 |
| WO | WO 2008/052277 A1 | 5/2008 |
| WO | WO 2010/088160 A1 | 8/2010 |
| WO | WO 2011/029126 A1 | 3/2011 |
| WO | WO 2012/038055 A1 | 3/2012 |

OTHER PUBLICATIONS

Di Bartolo, V. et al., "Binding of Human GM-CSF to Synthetic Peptides of the Alpha Subunit of Its Receptor," *Journal of Receptors and Signal Transduction*, 1996, 16(1-2):77-92.

Reynolds, Sandra R. et al., "HLA-Independent Heterogeneity of $CD8^+$ T Cell Responses to MAGE-3, Melan-A/MART-1, gp100, Tyrosinase, MC1R, and TRP-2 in Vaccine-Treated Melanoma Patients[1]," *The Journal of Immunology*, 1998, 161:6970-6976.

* cited by examiner

*Primary Examiner* — Alana Harris Dent
(74) *Attorney, Agent, or Firm* — Saliwanchik, Lloyd & Eisenschenk

(57) ABSTRACT

The present invention relates to novel tumor-associated antigens, which elicit independently from a presentation via MHC a CD8-positive T-cell response. GM-CSF-Receptor alpha chain (CSF2RA) and Tyrosinase-related protein 2 (TRP-2) were found to be targets of CD8-positive T-cell clones which could detect the proteins on the surface of HLA I negative melanoma cells. Thus, the invention provides proteins, protein fragments and polypeptides of the novel antigens for use in medicine, for example for the treatment, diagnosis and prevention of a tumor disease. Furthermore provided are nucleic acids expressing the antigens of the invention, binding agents specific for the antigens of the invention, such as T-cell receptor chains and isolated T cells which are reactive against the antigens of the invention or which express the T-cell receptors of the invention. The invention further pertains to pharmaceutical compositions, especially vaccine compositions, comprising the antigens, nucleic acids, binding agents or T cells in accordance with the invention, and methods for the generation of T cells, which are specifically reactive to the antigens of the invention in an MHC-independent manner.

2 Claims, 10 Drawing Sheets

| MEL | HLA-A | HLA-B | HLA-C |
|---|---|---|---|
| MEL-86A | -A*01:01<br>-A*24:02 | -B*08:01<br>-B*15:01 | -C*07:01<br>-C*03:03 |
| MEL-86B | - | - | - |
| MEL-86C | -A*01:01 | -B*08:01 | -C*07:01 |
| MEL-86F | - | - | - |

: negative for melanoma antigens

: positive for melanoma antigens

Figure 4:

| Donor-number Leucocyte concentrates | Target cells | 1A.1/506 |
|---|---|---|
| BC 1102546 | FastDC | |
| | monocytes | |
| BC 1102547 | FastDC | |
| | monocytes | |
| BC 1102549 | FastDC | |
| | monocytes | |
| BC 1103394 | granulocytes | |
| - | - | |
| | MA-MEL-86A | |
| | MA-MEL-86B | |
| | MA-MEL-86C | |

| | | V-Element | CDR1 | CDR2 | CDR3 | | J-Element |
|---|---|---|---|---|---|---|---|
| 1A.1/506 (HLA-independent recognition of CSF2RA) | α-chain | TRAV21*02 | DSAIYN | IQSSQRE | CA VGGNDYKLS | FG | TRAJ20*01 |
| | β-chain | TRBV10-3*01 | ENHRY | SYGVKD | CA ISEKLAGAYEQY | FG | TRBJ2-7*01 |

Figure 11:

|   | 293T | Transfected cDNA | 2C/417 |
|---|---|---|---|
| A | + | TRP-2 TMD*del* | |
|   | + | TRP-2 *fl* | |
|   | + | - | |

|   | 293T | Transfected cDNA | 2C/417 |
|---|---|---|---|
| B | + | TRP-2 TMD*del* +HLA-A24 TMD | |
|   | + | TRP-2 *fl* | |
|   | + | - | |

C: TRP-2 TMD *del* — HLA-A*24:01 TMD / EcoRI

Figure 12:

| | | V-Element | CDR1 | CDR2 | CDR3 | | J-Element |
|---|---|---|---|---|---|---|---|
| 2C/417 (HLA-independent recognition of TRP2) | α-chain | TRAV3*01 | VSGNPY | YITGDNLV | CA VRDMIEGGGNKLT | FG | TRAJ10*01 |
| | β-chain | TRBV28*01 | MDHEN | SYDVKM | CAS SRQGAVGQPQH | FG | TRBJ1-5*01 |

Figure 13:
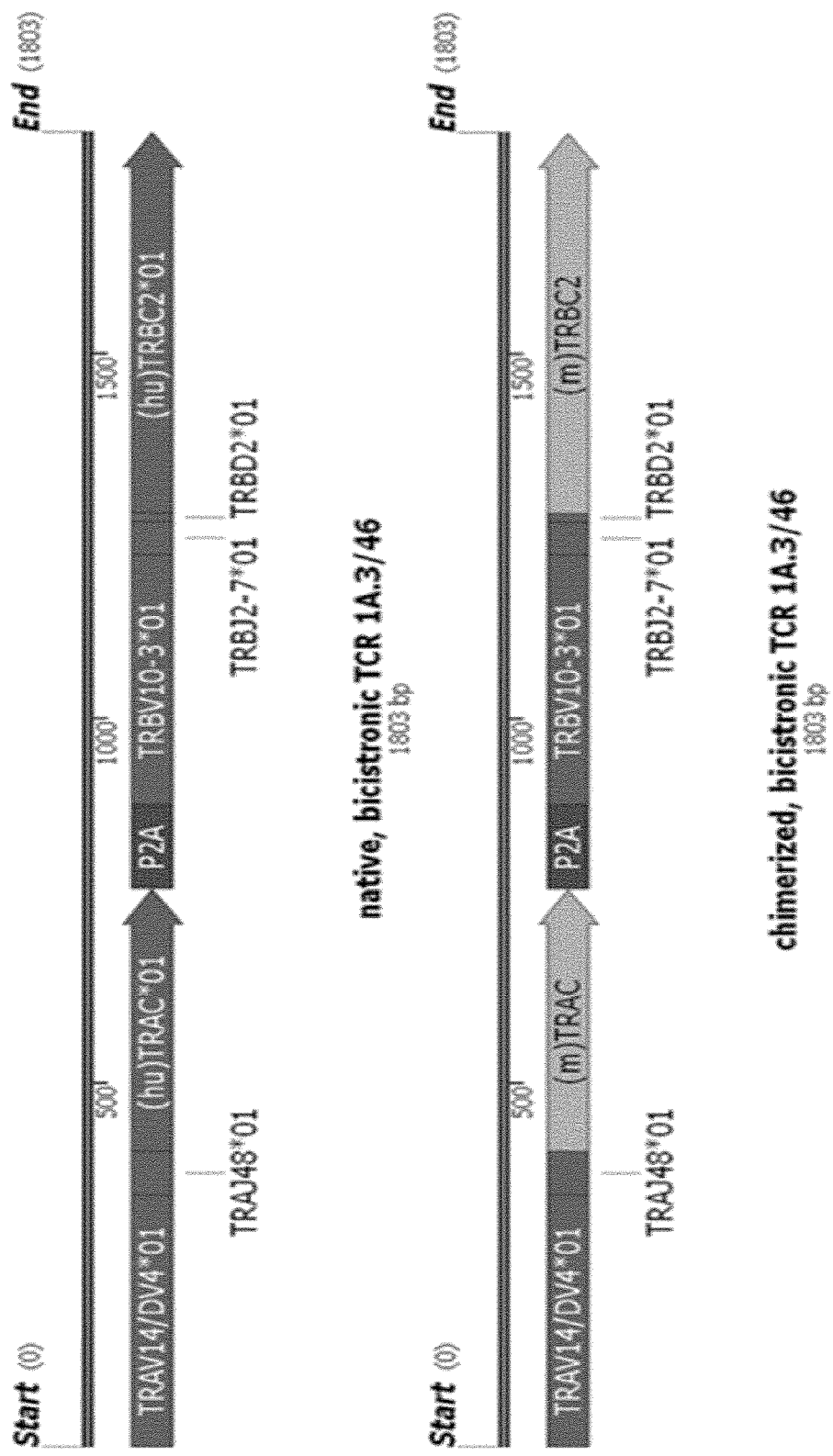

Figure 13 B and C:
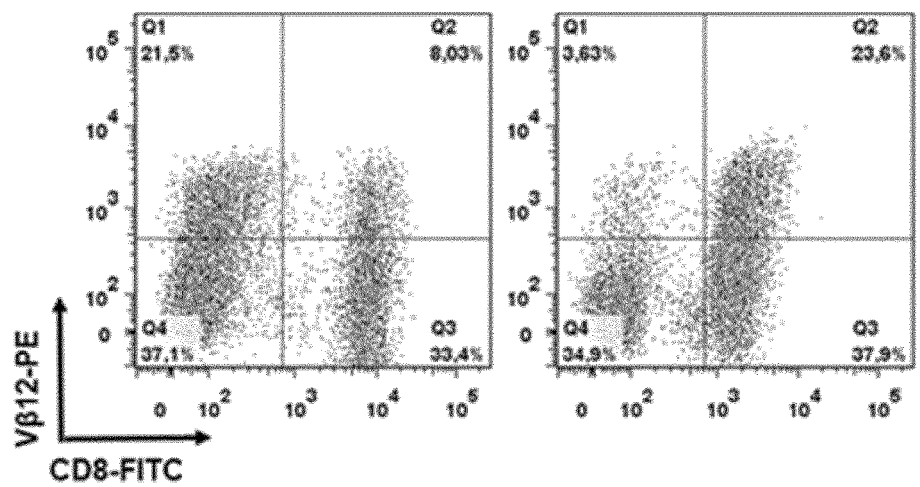
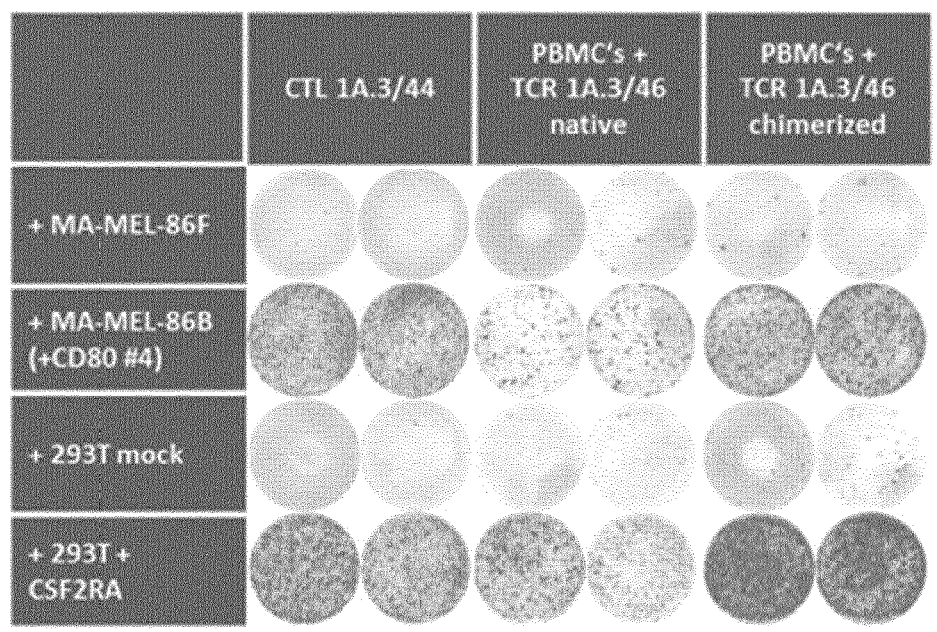

T CELL RECEPTORS WITH MHC INDEPENDENT BINDING TO GM-CSF RECEPTOR ALPHA CHAIN

CROSS REFERENCE TO A RELATED APPLICATION

This application is a National Stage Application of International Application Number PCT/EP2013/076760, filed Dec. 16, 2013; which claims priority to European Application No. 12197289.7, filed Dec. 14, 2012; both of which are incorporated herein by reference in their entirety.

The Sequence Listing for this application is labeled "SEQ-LIST-5-28-15.TXT", which was created on May 28, 2015, and is 26 KB. The entire content is incorporated herein by reference in its entirety.

FIELD OF THE INVENTION

The present invention relates to novel tumor-associated antigens, which elicit independently from a presentation via MHC a CD8 positive T-cell response. GM-CSF-Receptor alpha chain (CSF2RA) and Tyrosinase-related protein 2 (TRP-2) were found to be targets of CD8 positive reactive T-cell clones which could detect the proteins on the surface of HLA I negative melanoma cells. Thus, the invention provides proteins, protein fragments and polypeptides of the novel antigens for use in medicine, for example for the treatment, diagnosis and prevention of a tumor disease. Furthermore provided are nucleic acids expressing the antigens of the invention, binding agents specific for the antigens of the invention, such as T-cell receptor chains and isolated T cells which are reactive against the antigens of the invention or which express the T-cell receptors of the invention. The invention further pertains to pharmaceutical compositions, especially vaccine compositions, comprising the antigens, nucleic acids, binding agents or T cells in accordance with the invention, and methods for the generation of T cells specifically reactive to the antigens of the invention in an MHC-independent manner.

DESCRIPTION

Cancer is still the main cause of death albeit the development of many treatment strategies including extensive radiation and chemotherapy. Furthermore, it is known that tumor rejection mechanisms are mediated by autologous immune cells, especially T-cells, which are able to differentiate between cancerous cells and healthy cells by the detection of tumor-associated antigen (TAA)-fragments via major histocompatibility complex (MHC) presentation. Antigens which are specifically expressed in tumor cells and not in healthy tissue can be categorized into four types: (I) mutated antigens develop during tumorigenesis by point mutations or translocations within the tumor cells. Those antigens are strictly tumor-specific. (II) cancer/germline antigens are usually expressed solely within the germ cells of an adult organism and not in healthy somatic tissue. In cancer cells, however, due to the loss of epigenetic regulation, germ-cell specific genes can be activated. (III) differentiation antigens are expressed in tumors and their healthy progenitor cells. CTL responses against such antigens often result in auto-immune reactions. (IV) overexpressed TAA show only minor expression in healthy cells whereas in a tumor those antigens are strongly activated. Human tumors usually express antigens of different categories and might even process and present distinct peptides from each of these proteins via their respective HLA class I and class II molecules.

MHC molecules in humans are normally referred to as HLA (human leukocyte antigen) molecules. There are two principal classes of HLA molecules: class I and class II. CD8-positive T cells are usually cytotoxic (therefore named cytotoxic T cells=CTL), recognize peptides of 9 to 10 amino acids which are intracellularly processed from proteins of any subcellular localization and which are presented on the cellular surface by HLA class I molecules. In the field of human cancer immunology, the last two decades have seen intensive efforts to characterise cancer-associated and cancer-specific antigens. Also, effort has been devoted to the analysis of antibodies to human tumor antigens. Such antibodies can be used for diagnostic and therapeutic purposes, for instance in combination with an anti-cancer agent. In addition, promising approaches of vaccine therapies are currently developed based on MHC-class I antigenic fragments, there is still no satisfactory immune therapy available for most cancer types.

To date only few examples are known for HLA/MHC-independent recognition of TAA via CD4- or CD8-positive T cells. Barnd and co-workers, 1989 *PNAS*, described the recognition of epithelial mucin on breast and ovarian cancer cells. A HLA-independent recognition was further found for nickel-reactive CD8-positive T-cells in two patients suffering from contact dermatitis (Moulon et al., *J Invest Dermatol* 2003), for a melanoma-reactive T-cell clone without identifying the responsible antigen (Somasundaram et al., *J Transl Med* 2005) and for a kidney cell carcinoma-reactive T-cell clone (Wang et al., J Immunol 2008); the antigen of the latter was recently published (Hanada et al., *Blood* 2011).

Although a high number of HLA-restricted TAAs out of all four of the above mentioned categories were identified in the past, still no satisfactory treatment based on a therapeutic vaccination and adoptive transfer of antigen-specific T cells is available. This is in part due to problems with respect to reproducibility of the results in clinical studies or to the observation of an only insufficient clinical effect of the vaccine. A problem often encountered in cancer immunotherapy is further an impairment of the immunogenicity in cancer tissue. This so-called "immune escape" can be understood on the basis of phenotype differences encountered in neoplastic cells. For example, tumor cells show decreased ability to process and present antigens, have a decreased ability to stimulate autologous T cells, show complete downregulation of immunogenic proteins associated with transformed cells and/or no or low expression of leukocyte adhesion molecules or other accessory molecules and selective downregulation of certain MHC class I and class II alleles. The latter may affect all class I/II antigens, or only part of them. Partial HLA loss of function or expression can be caused by loss of single HLA alleles, HLA haplotypes or complete HLA class I loss due to bi-allelic β2m gene loss (Aptsiauri et al., *Cancer Immunol Immunother* 2008; Bernal M. et al. Cancer Immunol Immunother 61:1359-71, 2012). Tumors that have lost the expression of HLA are thus resistant to any treatment based on HLA-dependent T cells. Indeed, impairment of HLA function is one of the key "immune escape" mechanisms of tumor cells and thus limits the application of T-cell mediated immune therapy.

In view of the above described background art, the objective of the present invention is to provide novel tumor associated antigens (TAA) which allow for the development of novel treatments of cancer, and specifically novel treatments that circumvent the problem of immune escape in cancer cells.

In a first aspect of the present invention, the above objective is solved by providing a protein, protein fragment or polypeptide comprising at least 8 contiguous amino acids from the amino acid sequence of the GM-CSF-receptor alpha chain (CSF2RA) (SEQ ID No. 1) or the tyrosinase-related protein 2 (TRP-2) (SEQ ID No. 2), wherein said protein, protein fragment or polypeptide is capable of inducing a T-cell response and/or binding a cognate T-cell receptor.

In another embodiment of the invention, the protein, protein fragment or polypeptide comprises the amino acid sequence of a complex epitope of the native TRP-2 or CSF2RA proteins. A complex epitope in connection with the herein described invention is a binding site for an immunological binding agent, such as a T-cell receptor (TCR) or antibody, which is composed of two or more amino acid sequences which are in close spatial proximity in the native three-dimensional folded proteins, but which do not constitute one contiguous sequence within the linear amino acid sequence of the antigen. A complex epitope, for example, can be composed of stretches of the amino acid sequences of two spatially closely folded secondary structures within the antigen, or between two separate amino acid chains of contacting subunits of a multi protein complex.

The inventors surprisingly identified the proteins tyrosinase-related protein 2 (TRP-2) and GM-CSF receptor alpha chain (CSF2RA) as molecules expressed in melanoma (TRP-2) and other malignant cell types (CSF2RA), which are recognized by T cells in an HLA-independent manner. Thus, T cells against the antigens of the invention provide the surprising advantage to lyse tumors cells that are either completely negative for HLA class I expression, or at least show an impairment of HLA expression and/or function. Normally such cells would escape the patient's natural or a therapeutically induced immune rejection.

The protein, protein fragment or polypeptide of the invention in an additional embodiment comprises at least 10, preferably 15, 20, 50, and most preferably 100 contiguous amino acids from the amino acid sequence of GM-CSF-Receptor alpha chain (CSF2RA) (SEQ ID No. 1) or tyrosinase-related protein 2 (TRP-2) (SEQ ID No. 2), wherein said protein, protein fragment or polypeptide is capable of inducing a T-cell response and/or binding a cognate T cell receptor.

In the context of the present invention the terms "protein" or "polypeptide" are used interchangeably and denote a polymer composed of amino acid monomers joined by peptide bonds. A "peptide bond" is a covalent bond between two amino acids in which the α-amino group of one amino acid is bonded to the α-carboxyl group of the other amino acid. All amino acid or polypeptide sequences, unless otherwise designated, are written from the amino terminus (N-terminus) to the carboxy terminus (C-terminus). The terms "protein", "protein fragment" and "polypeptide" refer to a molecular chain of amino acids, and do not refer to a specific length of the product and if required can be modified in vivo or in vitro, for example by glycosylation, amidation, carboxylation or phosphorylation. Thus, inter alia peptides, oligopeptides and proteins are included within the definition of polypeptide.

Of course, functional derivatives and fragments of the polypeptide, summarized under the term "protein fragment", are also included in the present invention. Functional derivatives are meant to include polypeptides which differ in one or more amino acids in the overall sequence, which have deletions, substitutions, inversions, insertions or additions. Amino acid substitutions which can be expected not to essentially alter biological and immunological activities, have been described. Amino acid replacements between related amino acids or replacements which have occurred frequently in evolution are inter alia Ser/Ala, Ser/Gly, Asp/Gly, Asp/Asn, Ile/Val.

In addition, the term "functional derivatives" of these polypeptides also implies the addition salts of the polypeptides, amides of the polypeptides and specifically the C-terminal amides, esters and specifically the C-terminal esters and N-acyl derivatives specifically N-terminal acyl derivatives and N-acetyl derivatives.

In accordance with the present invention, the protein, protein fragment or polypeptide is in a preferred embodiment a protein, protein fragment or polypeptide comprising an amino acid sequence with at least 50%, 60%, 70%, 80%, 90%, 95%, most preferably 99% and even more preferably 100% sequence identity to the amino acid sequence of the proteins GM-CSF receptor alpha chain (CSF2RA) or tyrosinase-related protein 2 (TRP-2), specifically to the amino acid sequences as shown in SEQ ID No. 1 or 2.

In preferred embodiments protein fragments of the herein described antigens are immunogenic fragments, which still have the ability to induce an immunogenic response, preferably independent of MHC class I and/or II.

In preferred embodiments of the invention the protein, protein fragment or polypeptide consists of the amino acid sequence shown in SEQ ID No. 1 or 2.

The polypeptides according to the invention can be produced either synthetically or by recombinant DNA technology. Methods for producing synthetic polypeptides are well known in the art.

With the aid of the proteins, protein fragments or polypeptides in accordance with the invention cytotoxic and helper T cells can be generated, which develop an antigen-specific, MHC-independent cytotoxic activity against tumor cells expressing proteins, protein fragments or polypeptides of the invention and destroy them. Therefore, these polypeptides open up the possibility of an effective tumor therapy, in the course of which the suppression of an immune reaction, which is often observed in tumor patients, can be reversed.

The invention also relates to a fusion protein composed of one of the aforementioned proteins, protein fragments or polypeptides and of a second protein or polypeptide. Such fusion proteins are suitable for use as a diagnostic or therapeutic or prophylactic agent or generally for a detection and/or manipulation of T cells that recognize TRP-2 or CSF2RA, specifically independent of their presentation via MHC. For example, fusion proteins could be envisioned that consist of a carrier protein such as, for example, HSA, collagen or other proteins and one or more of the polypeptides of the invention. The polynucleotides coding for this fusion protein are also the subject matter of the present invention.

Further provided is the protein, protein fragment or polypeptide in accordance with the present invention, which is characterized by the presence of a signal peptide which mediates the cellular transport of the molecule, when expressed in a cell, to the outside of the cellular membrane. Signal peptides are known to the person of skill in the art. More preferably the protein, protein fragment or polypeptide in accordance with the present invention comprises a domain capable of anchoring the molecule of the invention to the cellular membrane. Such a domain could be a membrane anchor or a transmembrane domain.

In one embodiment the protein, protein fragment or polypeptide according to the invention is characterized in that it is capable of inducing a major histocompatibility complex (MHC) independent T-cell response, preferably a MHC class I independent T-cell response, or a MHC class I and II independent T-cell response; and/or the protein, protein fragment or polypeptide is characterized in that it is capable of binding a cognate T-cell receptor expressed by a MHC class I independent T cell or a MHC class I and II independent T cell.

Due to the surprising finding of the independence of the recognition of the molecules of the invention from HLA/MHC expression, it is one further preferred embodiment that the protein, protein fragment or polypeptide in accordance with the invention is not presented by MHC class I, or MHC class I and II. The protein, protein fragment or polypeptide of the invention is preferably expressed on the cellular surface without undergoing a fragmentation as it is known for the presentation of MHC-restricted antigens. Thus, the present invention shall in a preferred embodiment pertain to such a protein, protein fragment or polypeptide which, when expressed in an HLA/MHC-negative cell, still is able to induce a T-cell response.

In the context of the various embodiments described herein, a protein, protein fragment or polypeptide shall not be excluded from the scope of the invention just because in addition to its capability to mediate a HLA-independent T-cell response, it still can be processed and presented by the MHC/HLA pathway. Only in specific embodiments of the invention a protein, a protein fragment or polypeptide shall be excluded, when it consists of an MHC/HLA class I and/or II binding epitope.

One particularly preferred embodiment of the present invention relates to the protein, protein fragment or polypeptide according to the description herein before, for use in medicine, specifically for use in a method of treatment of the human or animal body by surgery or therapy, or diagnostic methods practised on the human or animal body.

Further provided according to the present invention is the protein, protein fragment or polypeptide as described herein, for use in the prevention, diagnosis or treatment of a proliferative disease, preferably wherein the proliferative disease is a tumor disease. A preferred tumor disease according to the invention is a tumor disease that is devoid of a functional MHC class I complex, or that is devoid of functional MHC class I and II complexes, specifically such tumors which do not express MHC class I, or do not express MHC class I and II. Hence, the protein, protein fragment or polypeptide as described herein are specifically for use in the prevention, diagnosis or treatment of a tumor which exhibit immune escape by alteration of the MHC class I and/or II presentation complex.

As used herein, the term "tumor" or "tumor disease" means both benign and malignant tumors or neoplasms and includes melanomas, lymphomas, leukemias, and sarcomas, illustrative examples of tumor tissues are cutaneous such as malignant melanomas and mycosis fungoides; hematologic tumors such as leukemias, for example, acute lymphoblastic, acute myelocytic, or chronic myelocytic leukemia; lymphomas such as Hodgkin's disease or malignant lymphoma; gynecologic tumors such as ovarian and uterine tumors; urologic tumors such as those of the prostate, bladder, or testis; soft tissue sarcomas, osseus, or non-osseous sarcomas, breast tumors; tumors of the pituitary, thyroid, and adrenal cortex; gastrointestinal tumors such as those of the esophagus, stomach, intestine, and colon; pancreatic and hepatic tumors; laryngeal papillomas/carcinomas and lung tumors.

In preferred embodiments the tumor to be treated, diagnosed or prevented is characterized by the expression of CSF2RA (SEQ ID No 1) and/or TRP-2 (SEQ ID No 2). Or tumors expressing homologs of the aforementioned antigens, wherein a homolog is characterized the sequence identity of at least 75, preferably 80, 90, or 95% compared to a sequence as shown in SEQ ID No. 1 or 2, respectively.

Furthermore, such tumors are preferred in accordance with the various embodiments of the invention which underwent, or are at risk of undergoing, immune escape mechanisms by altering the expression and/or function of the HLA complexes (either class I or II or both) within the tumor cell.

Preferred tumors of the present invention with respect of TRP-2 are tumors of the skin, preferably melanoma, or tumors of the central nervous system, preferably glioblastoma.

On the other hand preferred tumors (or malignancies) of the present invention with respect to CSF2RA are tumors of the skin, such as melanoma, hematological malignancies expressing CSF2RA, such as leukemia, and solid tumors expressing CSFRA, such as lung cancer, pancreatic cancer, colorectal cancer and ovarian cancer. Specifically preferred in another embodiment is that the malignancy which expresses CSF2RA does not express CSF2RB, or expressed CSF2RB to a significantly lower level than CSF2RA.

In a preferred embodiment of the present invention, the above described protein, protein fragment or polypeptide of the invention for use in medicine, or proteins used within the herein described specific methods, are the full length proteins of CSF2RA and/or TRP-2, possible with minor amino acid changes of preferably not more than 50, 40, 30, 20, preferably 10, most preferably 5 amino acid residues compared to the sequences shown in SEQ ID No. 1 or 2, respectively. Such sequence changes can be additions, deletions, substitutions, inversions, insertions or chemical modification of one or more amino acid residues.

In an additional aspect, the present invention further provides an isolated nucleic acid molecule, wherein said nucleic acid molecule (a) has a strand encoding for a protein, protein fragment or polypeptide according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences which are necessary for expressing the nucleic acid sequence corresponding to the protein, specifically for expression in a mammalian/human cell. The nucleic acid used can be contained in a vector suitable for allowing expression of the nucleic acid sequence corresponding to the peptide in a cell. However, the nucleic acids can also be used to transfect a presenting cell, which shall not be restricted to classical antigen-presenting cells such as dendritic cells, in such a way that they themselves produce the corresponding proteins on their cellular surface.

The nucleic acid molecules of the invention are preferably for use in medicine.

Also provided is a vector or a cell comprising a nucleic acid molecule described herein above, specifically wherein the vector is for use in medicine. Also a cell comprising a vector according to the invention is provided.

Another aspect of the present invention is the use of at least one protein, protein fragment or polypeptide in accordance with the invention or a nucleic acid in accordance with the invention for eliciting an immune reaction in connection with a tumor therapy or a treatment for preventing a tumor. Advantageous here is the fact that the frequently observed immune escape mechanisms and tolerance to TAA in a tumor disease can be overcome (or reversed) by the use of a protein, protein fragment or polypeptide, or nucleic acids in accordance with the invention. The use in accordance with the invention can also be employed in addition to established tumor therapies.

A preventive treatment in the context of the herein described invention is of benefit possibly mainly to persons who have an increased risk of developing a tumor, because, for example, they are hereditarily predisposed or because they have already had a tumor before. In another embodiment a preventive treatment is of benefit for a patient suffering from a tumor disease with increased risk of having developed or developing resistance to immune rejection, by e.g. immune escape via the alteration of the function and/or expression of HLA class I/II complexes.

Yet another aspect of the invention pertains to a binding agent, which binds to a protein, protein fragment or polypeptide as described herein above, preferably wherein the binding agent is specific for said protein, protein fragment or polypeptide. In preferred embodiments the binding agents as described herein are for use in medicine.

In one embodiment the binding agent according to the invention is an antibody, or a fragment thereof. The term "antibody" in its various grammatical forms is used herein to refer to immunoglobulin molecules and immunologically active portions of immunoglobulin molecules, i.e., molecules that contain an antibody combining site or a paratope. Such molecules are also referred to as "antigen binding fragments" of immunoglobulin molecules. Illustrative antibody molecules are intact immunoglobulin molecules, substantially intact immunoglobulin molecules and those portions of an immunoglobulin molecule that contain the paratope, including those portions known in the art as Fab, Fab', F(ab')2 and F(v). Antibodies of the present invention may be monoclonal or polyclonal. The term antibody is also intended to encompass single chain antibodies, chimeric, humanized or primatized (CDR-grafted) antibodies and the like, as well as chimeric or CDR-grafted single chain antibodies, comprising portions from two different species. Immunological adjuvants for vaccines comprising lecithin may be used to stimulate antibody production.

In another embodiment the binding agent of the invention is a T-cell receptor (TCR), or a fragment thereof. A TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The extracellular portion of native heterodimeric αβTCR consists of two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies.

In one preferred embodiment the TCR of the invention is characterized to comprise a sequence according to any one of SEQ ID No. 3 to 8, or having a sequence that is at least 75, preferably 80, 90, or 95% identical any one of SEQ ID No. 3 to 8. Also comprised are T cells which express TCRs having a sequence according to any one of SEQ ID No. 3 to 8, or having a sequence that is at least 75, preferably 80, 90, or 95% identical to SEQ ID No. 3 to 8.

An antigen binding agent of the invention, preferable a TCR or antibody, is in one embodiment characterized by the presence of any one of, or preferably all, CDR 1 to 3 sequences as depicted for the respective alpha or beta chains of the TCRs of the invention in the figures and table 1 below. In this embodiment it is also preferred that the TCR of the invention is a chimerized TCR, for example, by exchanging completely or in part the original human constant domain with a murine constant domain (see FIG. 13). A preferred murinization of the constant domain is the exchange of at least the extracellular part of the constant domain with murine sequences.

One embodiment of the present invention pertains to an antigen binding polypeptide comprising at least one CDR sequences, preferably CDR3, more preferably CDR1, CDR2 and CDR3, of any one of the TCR as isolated in context of the present invention and as depicted in table 1 below.

TABLE 1

CDR sequences of the T-cell receptor clones of the invention. SEQ ID NO are given in ( ):

| Target | TCR Chain: | CDR1 | CDR2 | CDR3 |
| --- | --- | --- | --- | --- |
| CSF2RA | 1A.1/506 alpha | DSAIYN(9) | IQSSQRE(10) | CAVGGNDYKLS(11) |
| CSF2RA | 1A.1/506 beta | ENHRY(12) | SYGVKD(13) | CAISEKLAGAYEQY(14) |
| TRP2 | 2C/417 alpha | VSGNPY(15) | YITGDNLV(16) | CAVRDMIEGGGNKLT(17) |
| TRP2 | 2C/417 beta | MDHEN(18) | SYDVKM(19) | CASSRQGAVGQPQH(20) |
| CSF2RA | 1A3/46 alpha | TSDPSYG(21) | QGSYDQQN(22) | CAMRPHFGNEKLT(23) |
| CSF2RA | 1A3/46 beta | ENHRY(24) | SYGVKD(25) | CAISEKLAGAYEQY(26) |

The antigen binding polypeptide of the invention is preferably a TCR.

Thus also preferred is a T cell receptor alpha chain comprising any one, or all of, of the SEQ ID NO: 9 to 11, or 15 to 17, or 21 to 23.

Thus also preferred is a T cell receptor beta chain comprising any one, or all of, of the SEQ ID NO: 12 to 14, or 18 to 20, or 24 to 26.

Preferably a T-cell receptor of the invention, or a binding fragment thereof, has an alpha chain variable region comprising the CDR sequences of SEQ ID NO: 9, 10 and/or 11, and a beta chain variable region comprising the CDR sequences of SEQ ID NO: 12, 13 and/or 14. Such a TCR is a TCR specific for the antigen CSF2RA. Preferably this TCR is the TCR as isolated from the CTL 1A.1/506 as described herein in the examples. Such a receptor may in one embodiment comprise the at least variable region, preferably full length, sequence according to SEQ ID No. 3 (alpha chain) and 4 (beta chain).

Preferably a T-cell receptor of the invention, or a binding fragment thereof, has an alpha chain variable region comprising the CDR sequences of SEQ ID NO: 21, 22 and/or 23, and a beta chain variable region comprising the CDR sequences of SEQ ID NO: 24, 25 and/or 26. Such a TCR is a TCR specific for the antigen CSF2RA. Preferably this TCR is the TCR as isolated from the CTL 1A3/46 as described herein in the examples. Such a receptor may in one embodiment comprise the at least variable region, preferably full length, sequence according to SEQ ID No. 7 (alpha chain) and 8 (beta chain).

Preferably a T-cell receptor, or a binding fragment thereof, has an alpha chain variable region comprising the CDR sequences of SEQ ID NO: 15, 16 and/or 17, and a beta chain variable region comprising the CDR sequences of SEQ ID NO: 18, 19 and/or 20. Such a TCR is a TCR specific for the antigen TRP2. Preferably this TCR is the TCR as isolated from the CTL 2C/417 as described as described herein in the examples. Such a receptor may in one embodiment comprise the at least variable region, preferably full length, sequence according to SEQ ID No. 5 (alpha chain) and 6 (beta chain).

Yet another embodiment of the invention pertains to a single chain TCR (scTCR) as a binding agent, preferably an αβ-scTCR. Single-chain TCRs (scTCRs) are artificial constructs consisting of a single amino acid strand. An scTCR can comprise a polypeptide of a variable region of a first TCR chain (e.g., an [alpha] chain) and a polypeptide of an entire (full-length) second TCR chain (e.g., a [beta] chain), or vice versa. Furthermore, the scTCR can optionally comprise one or more linkers which join the two or more polypeptides together. The linker can be, for instance, a peptide which joins together two single chains, as described herein. Such a scTCR may be composed of any of the variable and/or constant region as provided herein.

Also provided is such a scTCR of the invention, which is fused to a human cytokine, such as IL-2, IL-7 or IL-15.

The binding agent according to the invention can also be provided in the form of a multimeric complex, comprising at least two scTCR molecules, wherein said scTCR molecules are each fused to at least one biotin moiety, and wherein said scTCRs are interconnected by biotin-strepavidin interaction to allow the formation of said multimeric complex. Also provided are multimeric complexes of a higher order comprising more than two scTCR of the invention.

In another preferred embodiment the binding agents of the invention is a bi-specific monoclonal antibody comprising the binding fragments of an antibody as described herein above, and the binding fragments of a second antibody which is, for example, specific for CD3.

Another aspect of the present invention pertains to a nucleic acid encoding a TCR or antigen binding agent as described herein.

In a further aspect, the objective of the present invention is solved by providing a T cell which is reactive against any one of the proteins, protein fragments or polypeptides according to the invention, specifically against CSF2RA or TRP-2. In a preferred embodiment, the T-cell of the invention is reactive against the protein, protein fragment or polypeptide according to the invention independent of the presentation of said protein, protein fragment or polypeptide by MHC class I and/or class II. An even more preferred embodiment of the invention provides a T cell comprising a T-cell receptor (TCR) which binds to a protein, protein fragment or polypeptide according to the invention, and wherein said binding is independent of the presentation of said polypeptide by MHC class I or MHC class I and II. The T cell of the invention is preferably CD8 and/or CD4 positive.

Further provided according to the present invention is the use of a protein, protein fragment or polypeptide as described above, a nucleic acid as described above, a vector or cell as described above, a binding agent as described above, a T cell as described above, a multimeric complex as described above, in the preparation of a medicament for treating cancer, or in the preparation of a diagnostic for diagnosing cancer. The cancer may be a mammalian cancer. In particular, the cancer may be human cancer. For example, the cancer may be breast cancer, prostate cancer, pancreatic cancer, colorectal cancer, lung cancer, malignant melanoma, leukaemia, lymphoma, ovarian cancer, cervical cancer or a biliary tract carcinoma. Specifically preferred cancers are melanoma, glioblastoma or leukemia. Said medicament may be a vaccine.

In another aspect the objective of the invention is further solved by an in-vitro method for generating MHC-independent T-cells, comprising the steps of
  i. providing a first cell, preferably a tumor cell, that expresses a protein, protein fragment or polypeptide according to the invention as described herein above, preferably wherein the polypeptide is a full-length CSF2RA or TRP-2,
  ii. bringing a population of peripheral blood mononuclear cells (PBMCs) into contact with said first cell, and thereby stimulating said PBMCs, and
  iii. selecting out of the population of stimulated PBMCs T cells which have the ability to recognize (or which are reactive against) a cell expressing the protein, protein fragment or polypeptide used in (i), independent of the expression of MHC in said cell.

In this aspect, the MHC is preferably MHC class I and/or class II.

In one preferred embodiment of the method described above, said tumor cell and said PBMCs are autologous cells derived from one tumor patient. This embodiment has the advantage that MHC independent T cells can be generated for a tumor patient. Such T cells are usable for re-injection into the patient as a treatment-agent against the tumor the patient is suffering from.

The above described method in one preferred embodiment comprises as said first cell a cell that does not express MHC class I, or MHC class I and II, or that is at least impaired in MHC class I and/or II function and/or expression.

Yet a further preferred embodiment of the above described method is, when in step (iii) said ability of a T cell to recognize a cell expressing the protein, protein fragment or polypeptide used in (i) independent of the expression of MHC in said cell, is determined by testing the reactivity of said T cell against said cell expressing the protein, protein fragment or polypeptide, wherein
  (a) said cell expressing the protein, protein fragment or polypeptide is devoid of MHC class I or MHC class I and II, and/or (b) said T cell is tested for its reactivity against said cell expressing the protein, protein fragment or polypeptide in the presence of antibodies against MHC class I or II; and/or (c) said T cell is tested for its reactivity against xenogenic cells transfected with DNA or RNA encoding the protein, protein fragment or polypeptide, wherein in (a), (b) and/or (c) a T cell that shows reactivity is a T cell having the ability to recognize a cell expressing the protein, protein fragment or polypeptide used in (i) independent of the expression of HLA/MHC in said cell.

Also provided are T cells which are generated by a method according to the invention as described herein above. Preferably, the T cell of the invention is for use in medicine. Specifically, the T cell of the invention is for treating a patient suffering from a malignant disease by infusing said T cells into said patient, preferably wherein said T cells are derived from autologous PBMCs of said patient.

A further aspect pertains to a pharmaceutical composition, comprising a protein, protein fragment or polypeptide according to the invention, or a nucleic acid, a vector, a cell, a binding agent or an isolated T cell according to the invention. In a preferred embodiment the pharmaceutical composition is a vaccine.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Suitable adjuvants are, for example, aluminium hydroxide, phosphate or oxide, oil-emulsions (e.g. of Bayol F<(R)> or Marcol 52<(R)>), saponins or vitamin-E solubilisate.

The vaccine according to the present invention can be given inter alia intravenously, intraperitoneally, intranasally, intradermally, subcutaneously or intramuscularly.

The useful effective amount to be administered will vary depending on the age and weight of the patient and mode of administration of the vaccine.

The vaccine can be employed to specifically obtain a T-cell response, but it is also possible that a B-cell response is elicited after vaccination. If so, the B-cell response leads to the formation of antibodies against the protein, protein fragment or polypeptide of the vaccine, which antibodies will be directed to the source of the antigen production, i.e. the tumor cells. This is an advantageous feature, because in this way the tumor cells are combated by responses of both the cellular and the humoral arm of the immune system.

Both arms of immunological defense will even be more effectively triggered when the vaccine comprises the antigens of the invention in an antigen-presenting cell, independent of MHC expression. Antigen presentation can be achieved by using monocytes, macrophages, interdigitating cells, Langerhans cells and especially dendritic cells, loaded with one of the antigens of the invention.

It is also possible to use cells already transfected with a cloning vehicle harbouring the information for the antigens of the invention. These cells will act as antigen-presenting cells and will present the full-length antigens of the invention, or fragments thereof, on their surface in an MHC-independent manner. Thus, in the context of the present invention it is preferred to express the antigens of the invention such, that they are transported to the cellular surface of the antigen-presenting cell.

Instead of a vaccination with these cells, which next to the desired expression products also harbour many elements which are also expressed and which can negatively affect the desired immunogenic reaction of the cell, it is also possible that a vaccine is composed of liposomes which are loaded with the proteins, protein fragments and polypeptides of the invention, and which thus expose these antigens to the host immune system. Such liposomes, for instance, are filled with lymphokines. Such liposomes will trigger an immunological T-cell reaction.

By presenting the protein, protein fragment or peptide in the same way as it is also presented in vivo, an enhanced T-cell response will be evoked. Furthermore, by the natural adjuvant working of the relatively large antigen-presenting cells also a B-cell response is triggered.

This B-cell response will a.o. lead to the formation of antibodies directed to the native antigen. This complex is especially found in tumor cells, where it has been shown that the antigens of the invention are presented naturally, which are thus able to elicit a T-cell response. It is this naturally occurring phenomenon which is enlarged by the vaccination with cells already presenting the proteins, protein fragments or peptides of the invention. By enlarging not only an enlarged T-cell response will be evoked, but also a B-cell response will be initiated which leads to antibodies directed against the MHC-independent peptide.

The vaccines according to the invention can be enriched by numerous compounds which have an enhancing effect on the initiation and the maintenance of both the T-cell and the B-cell response after vaccination.

In this way addition of cytokines to the vaccine will enhance the T-cell response. Suitable cytokines are for instance interleukins, such as IL-2, IL-4, IL-7, IL-15 or IL-12, GM-CSF, RANTES, tumor necrosis factor and interferons, such as IFN-$\alpha$, -$\beta$, or -$\gamma$.

In a similar way, antibodies against T-cell surface antigens, such as CD2, CD3, CTLA-4, PD-1, CD27 and CD28 will enhance the immunogenic reaction.

Also the addition of helper epitopes to stimulate CD4<+> helper cells or CD8<+> killer cells augments the immunogenic reaction. Alternatively also helper epitopes from other antigens can be used, for instance from heat shock-derived proteins or cholera toxin.

Finally, the present invention relates to a method of treating a patient suffering from a tumor disease, comprising the administration of a therapeutically effective amount of at least one protein, protein fragment or polypeptide in accordance with the invention and/or at least one nucleic acid and/or at least one binding agent and/or at least one vector molecule and/or at least one T cell of the invention in an amount sufficient to achieve a therapeutic effect. Another aspect is a method of eliciting a tumor-specific CTL response comprising the administration of a response-eliciting amount of the MHC independent antigens in accordance with the invention (the proteins, protein fragments and polypeptides of the invention). Target malignancies are those expressing CSF2RA and TRP-2.

Figure 1:
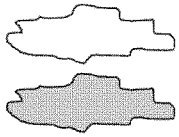
Figure 1:
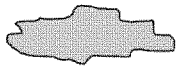

The present invention will now be further described in the following examples with reference to the accompanying figures and sequences, nevertheless, without being limited thereto. For the purposes of the present invention, all references as cited herein are incorporated by reference in their entireties. In the Figures and Sequences:

FIG. 1: HLA class I-phenotyping of melanoma cell lines MA-MEL-86A, -86B, -86C und -86F, generated from distinct lymph node metastases of patient MA-MEL-86 (schematic representation). MEL-86A expresses all HLA class I alleles of the patient but turned out to be negative for the expression of melanocyte differentiation antigens. Bi-allelic inactivations of the beta2-microglobulin ($\beta$2m) genes due to different mutations resulted in a complete loss of surface expression of HLA molecules in MA-MEL-86B and -F. MA-MEL-86C has lost expression of one (the "blue") HLA class I haplotype.

Figure 2:
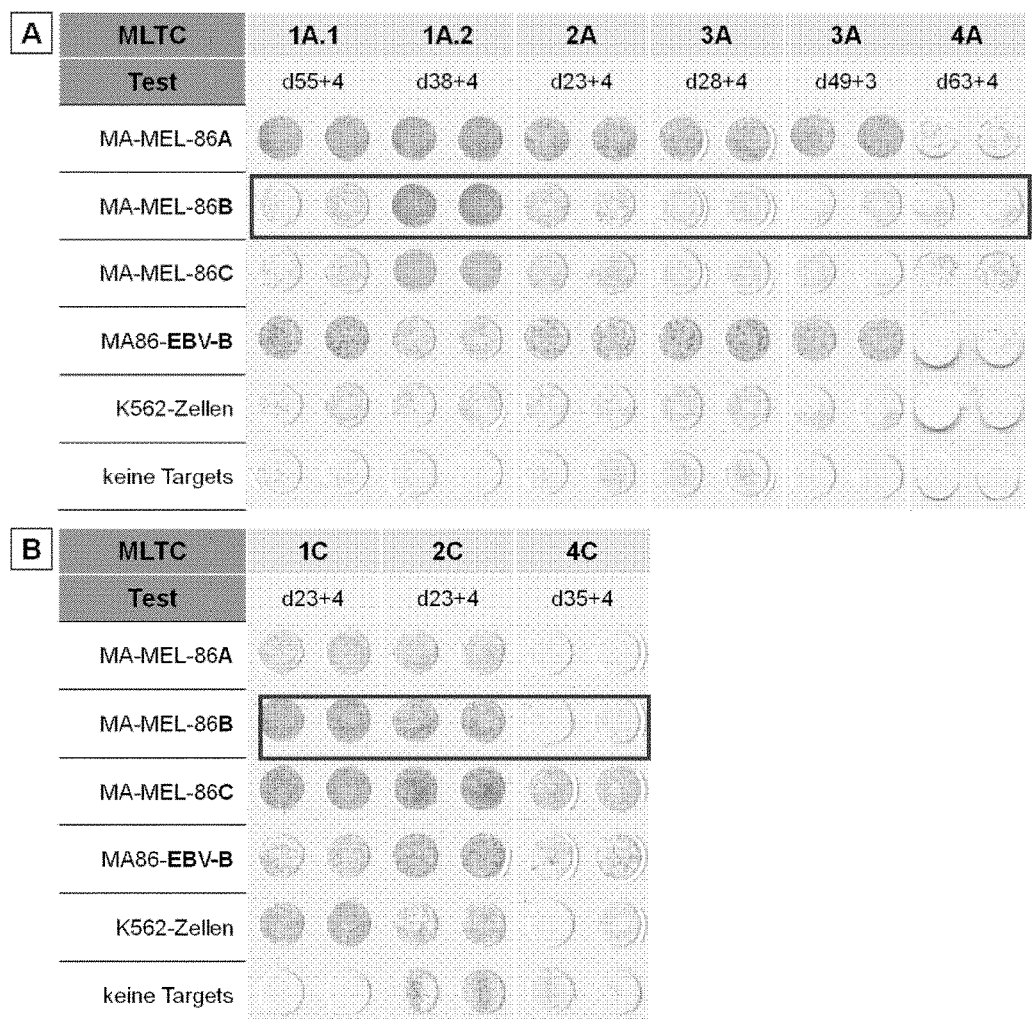

FIG. 2: Recognition of different MA-MEL-86 melanoma lines by independently generated Mixed Lymphocyte-Tumor cell Cultures (MLTC). Several different MLTCs were generated by stimulation of peripheral blood mononuclear cells (PBMC) with either melanoma line MA-MEL-86A (A) or -86C (B). MLTC responders (20.000/well) were then tested for recognition of MA-MEL-86A, -86B and -86C (50.000 cells/well) as well as control cell lines by use of 20h-IFN-γ-ELISpot-Assays.

Figure 3:
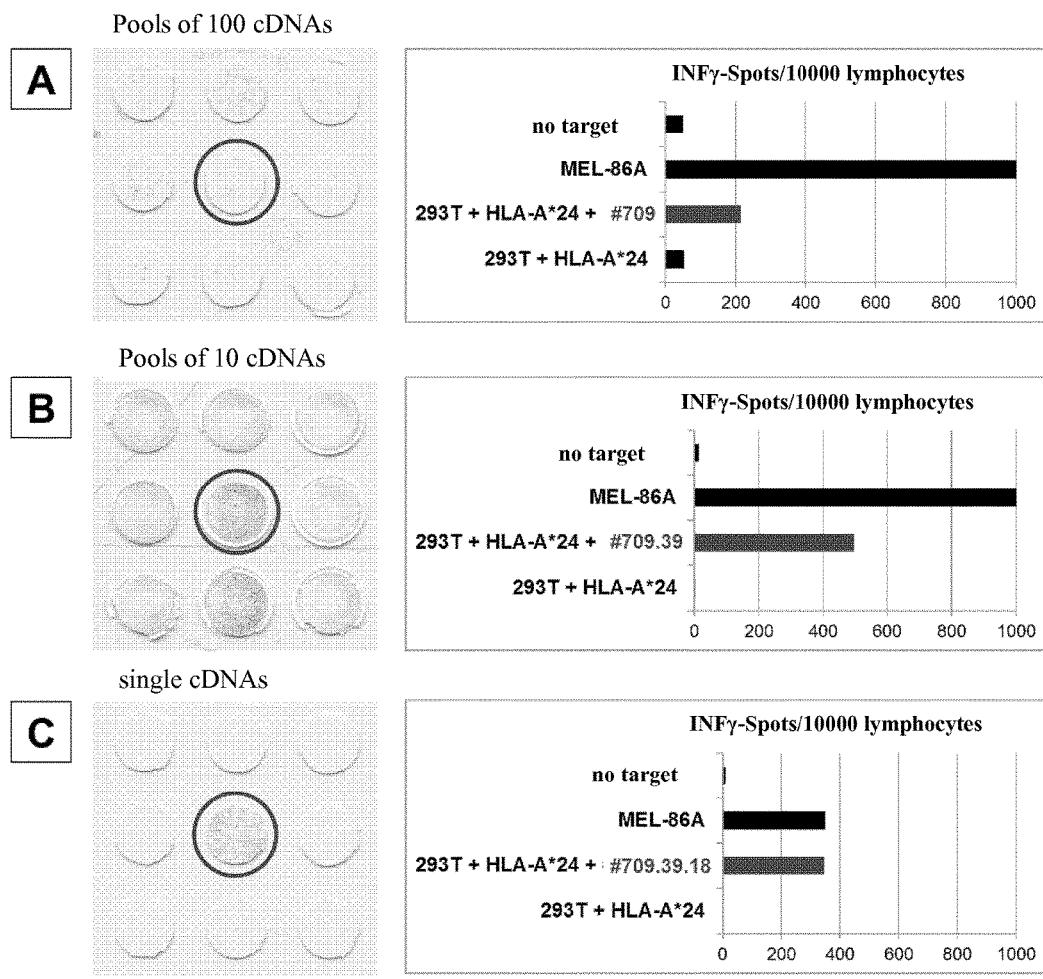

FIG. 3: cDNA-library-screening using MLTC 1A.1. MLTC 1A.1 was applied to the screening of the cDNA expression library constructed from the MA-MEL-86A cell line. Left part: Pictures show magnified sections of ELISpot plates containing positive wells. Right part: Diagrams showing the results of the analyses of the assays. (A) Section of the ELISpot plate testing of pools of 100 cDNAs per well comprising pools #701-796. After co-transfection of these cDNA pools together with HLA-A*24:02-cDNA into 293T cells, MLTC 1A.1 recognized transfectants expressing pool #709 (red circle). Pools of 10 cDNAs per well derived from 100× pool #709 tested in the same way identified pools #39 and #51 as being recognized by the T cells (B). Pool #39 was chosen for further subcloning. The subsequent testing of cDNA clones 709.39.1 to 709.39.96 identified cDNA-clone #18 as being recognized by MLTC 1A.1 (C). Targets: 293T cells (20.000 cells/well), MA-MEL-86A (50.000 cells/well); T cells: MLTC 1A.1 (10.000 lymphocytes/well); transfected cDNAs: HLA-cDNA (100 ng/well); cDNA pools (300 ng/well); 20h-IFN-γ-ELISpot-Assay. Sequencing of cDNA clone #709.39.18 and Blast search with the derived sequences identified CSF2RA (the alpha chain of the GM-CSF-receptor) as recognized antigen. The 1.831 bp long ORF of the #709.39.18-cDNA encodes for the transcript variant 2 of the gene, the translation of which results in the isoform A of the CSF2RA protein.

FIG. 4: Responses of CSF2RA-reactive CTL 1A.1/506 to different myeloid cells isolated from Buffy Coats (BC) of healthy donors. CTL 1A.1/506 (40,000 cells/well) was tested for recognition of Monocytes, Granulocytes and Dendritic cells (DC) (50,000 cells/well), the latter isolated and differentiated in vitro from PBMC of BC of four different healthy donors. The autologous melanoma lines served as controls.

Figure 5:
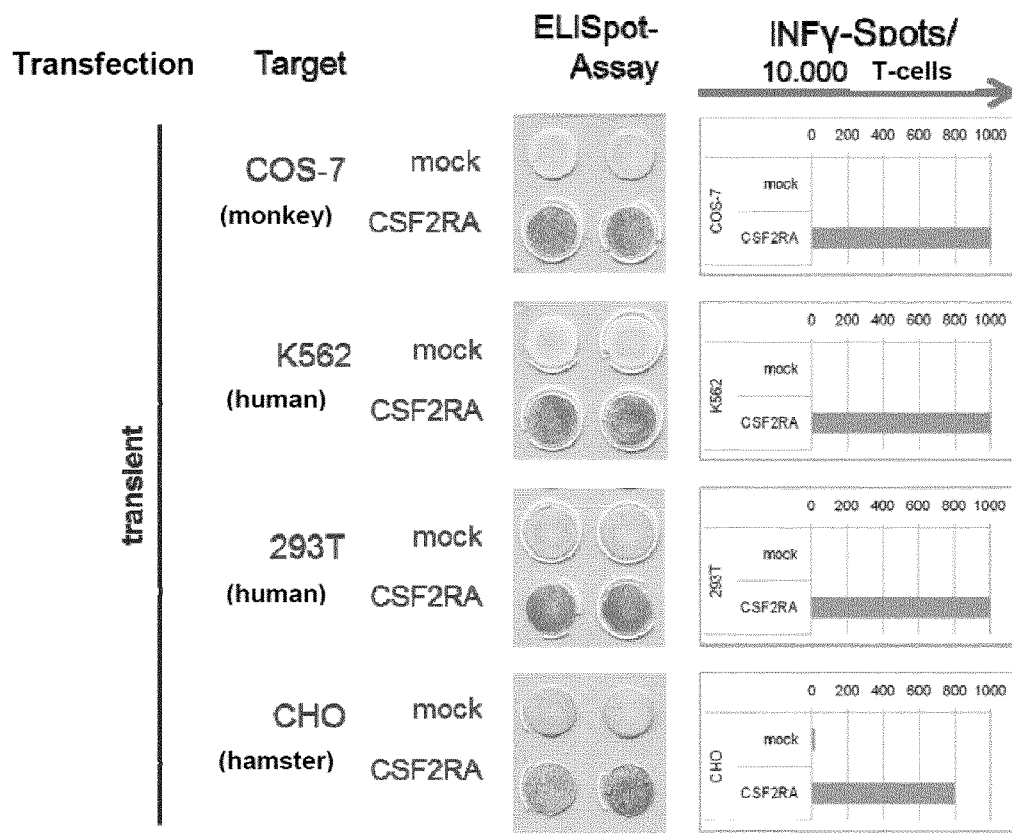

FIG. 5: Recognition of cells of various species after transfection with CSF2RA by CTL 1A.1/506. Human (K562, 293T), monkey (COS-7), and chinese hamster ovary (CHO) cells were transiently transfected with CSF2RA and tested for recognition by CTL 1A.1/506 using the IFN-γ ELISpot assay. All reactions were tested in duplicates.

Figure 6:
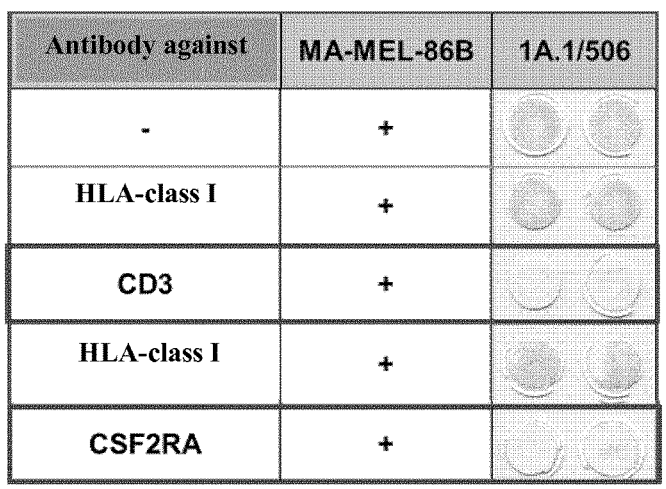

FIG. 6: Tumor recognition by CTL 1A.1/506 with and without blocking antibodies.

CTL 1A.1/506 (10.000 cells/well) was tested with an IFN-γ-ELISpot-assay for the recognition of MA-MEL-86B (50.000 cells/well). Monoclonal antibodies (mAbs) specific for pan-HLA I, CD3 or CSF2RA were applied to block recognition. Only mAbs binding to CSF2RA or the T-cell receptor (CD3) inhibited the CTL response.

Figures 7, 8:
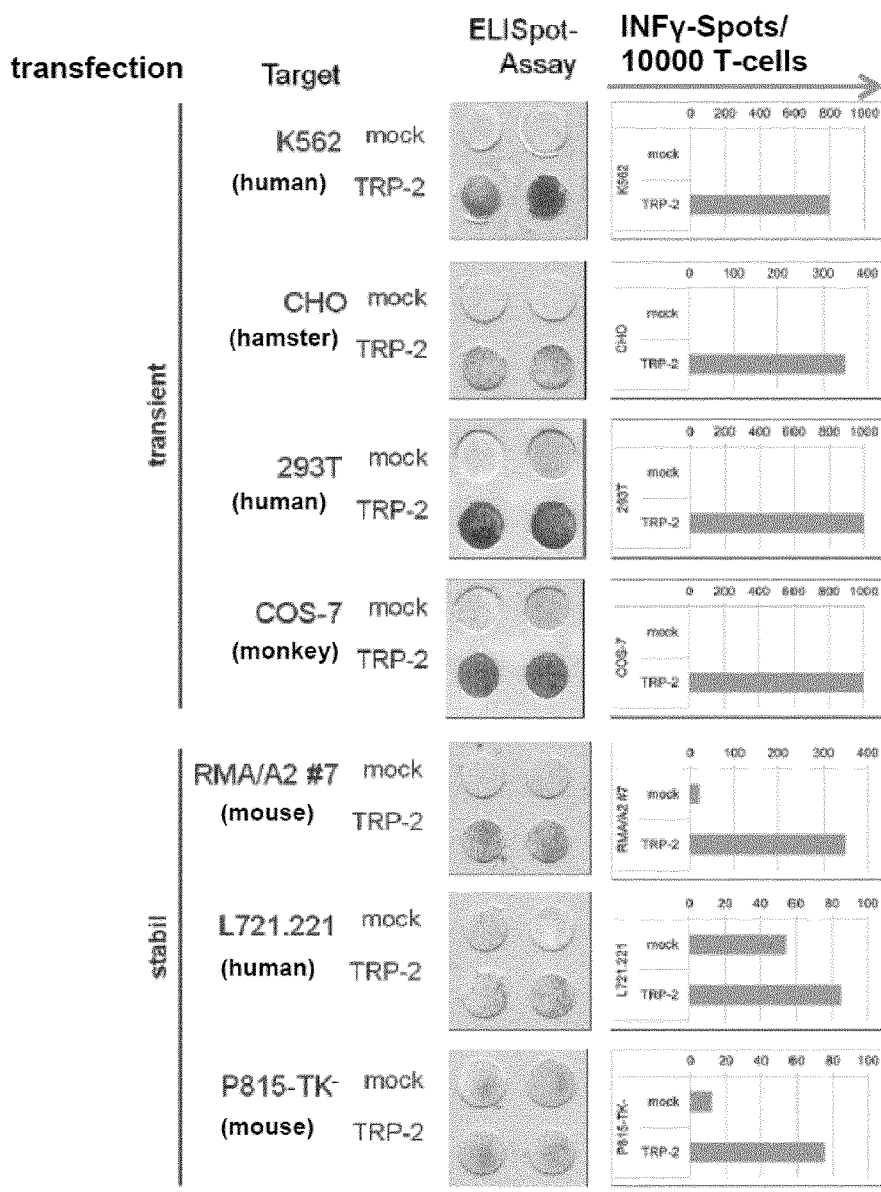

FIG. 7: Cloning of the T-cell receptor (TCR) of CTL 1A.1/506. Cloning of the TCR α- and β-chains was done according to the protocol published by Birkholz et al. (J Immunol Meth, 2009). TCR cDNA clones were sequenced and analyzed using the IMGT/VQuest database. TCR beta chains are composed of V (Variability)-, D (Diversity)- and J (Joining)-segments, while alpha chains are made up by V and J regions only. CDR (complementarity determining regions).

FIG. 8: Recognition of cells of various species after transfection with TRP-2 by CTL 2C/417. Human (K562, 293T, L721.221), monkey (COS-7), mouse (RMA/A2 #7, P815-TK-), and chinese hamster ovary (CHO) cells were transiently transfected with TRP-2 and tested for recognition by CTL 2C/417 using the IFN-γ ELISpot assay. All reactions were tested in duplicates.

Figure 9:
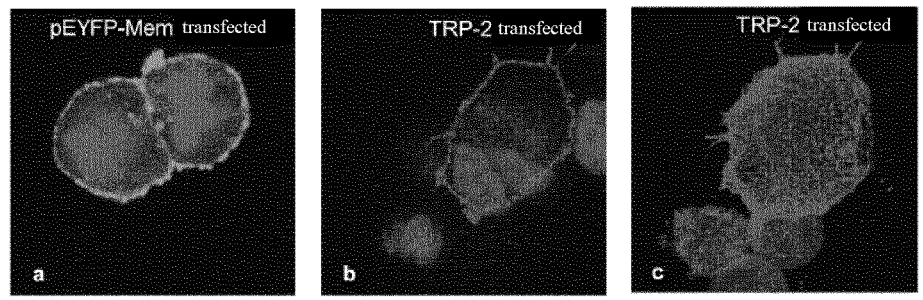

FIG. 9: Detection of TRP-2 surface expression by Confocal Laser Scanning Microscopy. 293T cells transfected with plasmids encoding membrane-bound pEYFP-Mem (a) and human TRP-2 were cultured on microscope slides. TRP-2 was detected with an Alexa 564-labeled polyclonal antibody against TRP-2 (b). The 3D confocal picture revealed that TRP-2 was detected as a transmembrane protein by this antibody (c).

Figure 10:
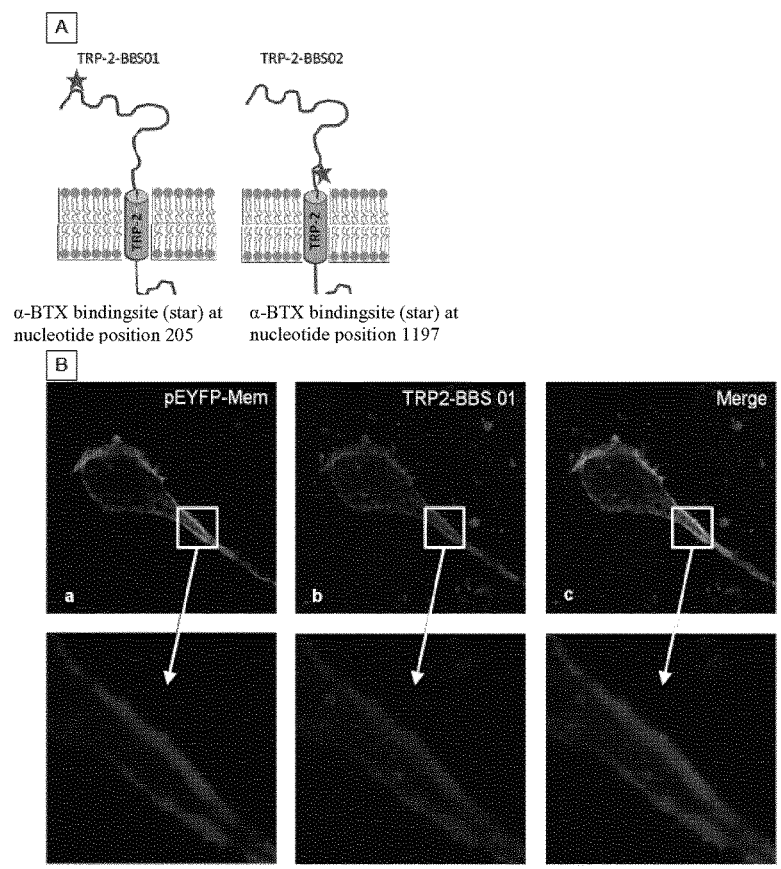

FIG. 10: Detection of TRP-2 surface expression by Confocal Laser Scanning Microscopy using a TRP-2-α-BTX fusion protein. The 13 amino acids long α-BTX binding site binds α-Bungarotoxin with high affinity. An α-BTX-binding site encoding sequence was integrated at different positions in the sequence coding for the extracellular portion of TRP-2 (A). MA-MEL-86A cells, cultured on microscope slides, were transiently co-transfected with a plasmid encoding the cell membrane tracking reagent pEYFP-Mem (a) and the TRP-2/αBTX-fusion protein. After staining with fluorescently labeled α-Bungarotoxin (red fluorescence, b), and overlaying the two pictures, the cell surface expression of the fusion protein became evident (yellow fluorescence, c).

FIG. 11: Recognition of TRP-2 by CTL 2C/417 requires that the protein contains a transmembrane domain (TMD). Full length (fl) TRP-2 cDNA or a TRP-2 variant lacking the TMD-coding sequence of the protein (TMDdel) were transfected into 293T cells and tested for recognition by CTL 2C/417 via the IFN-γ ELISpot assay. The deletion variant was not recognized (A). When the original TMD-coding sequence was replaced by the TMD cloned from the HLA-A24-cDNA and this replacement variant was transfected in comparison with the TRP-2 fl-cDNA into 293T cells, the CTL recognized both variants (B). This result further confirms that TRP-2 needs to be displayed on the cell surface to become recognized by the T cells. (C) Schematic representation of the recombinant TRP-2 containing the HLA-A24-TMD.

FIG. 12: Cloning of the T cell receptor (TCR) of CTL 2C/417. Cloning of the TCR α- and β-chains was done according to the protocol published by Birkholz et al. (J Immunol Meth, 2009). TCR cDNA clones were sequenced and analyzed using the IMGT/VQuest database. TCR beta chains are composed of V (Variability)-, D (Diversity)- and J (Joining)-segments, while alpha chains are made up by V and J regions only. CDR (complementarity determining regions).

FIGS. 13A-13C: shows cloning expression and analysis of a native and chimerized TCR isolated from CTL 1A.3/46.

SEQ ID NO. 1 shows the amino acid sequence of CSF2RA:

MLLLVTSLLLCELPHPAFLLIPEKSDLRTVAPASSLNVRFDSRTMNLSWD

CQENTTFSKCFLTDKKNRVVEPRLSNNECSCTFREICLHEGVTFEVHVNT

SQRGFQQKLLYPNSGREGTAAQNFSCFIYNADLMNCTWARGPTAPRDVQY

FLYIRNSKRRREIRCPYYIQDSGTHVGCHLDNLSGLTSRNYFLVNGTSRE

IGIQFFDSLLDTKKIERFNPPSNVTVRCNTTHCLVRWKQPRTYQKLSYLD

FQYQLDVHRKNTQPGTENLLINVSGDLENRYNFPSSEPRAKHSVKIRAAD

-continued
VRILNWSSWSEAIEFGSDDGNLGSVYIYVLLIVGTLVCGIVLGFLFKRFL

RIQRLFPPVPQIKDKLNDNHEVEDEIIWEEFTPEEGKGYREEVLTVKEIT

SEQ ID NO. 2 shows the amino acid sequence of TRP-2 (isoform 1)

MSPLWWGFLLSCLGCKILPGAQGQFPRVCMTVDSLVNKECCPRLGAESAN

VCGSQQGRGQCTEVRADTRPWSGPYILRNQDDRELWPRKFFHRTCKCTGN

FAGYNCGDCKFGWTGPNCERKKPPVIRQNIHSLSPQEREQFLGALDLAKK

RVHPDYVITTQHWLGLLGPNGTQPQFANCSVYDFFVWLHYYSVRDTLLGP

GRPYRAIDFSHQGPAFVTWHRYHLLCLERDLQRLIGNESFALPYWNFATG

RNECDVCTDQLFGAARPDDPTLISRNSRFSSWETVCDSLDDYNHLVTLCN

GTYEGLLRRNQMGRNSMKLPTLKDIRDCLSLQKFDNPPFFQNSTFSFRNA

LEGFDKADGTLDSQVMSLHNLVHSFLNGTNALPHSAANDPIFVVLHSFTD

AIFDEWMKRFNPPADAWPQELAPIGHNRMYNMVPFFPPVTNEELFLTSDQ

LGYSYAIDLPVSVEETPGWPTTLLVVMGTLVALVGLFVLLAFLQYRRLRK

GYTPLMETHLSSKRYTEEA

SEQ ID NO. 3 shows the TCR alpha chain sequence of CTL 1A.1/506

METLLGPLILWLQLQWVSSKQEVTQIPAALSVPEGENLVLNCSFTDSAIY

NLQWFRQDPGKGLTSLLLIQSSQREQTSGRLNASLDKSSGRSTLYIAASQ

SGDSATYLCAVGGNDYKLSFGAGTTVTVRANIQNSDPAVYQLRDSKSSDK

SVCLFTDFDSQTNVSQSKDSDVYITDKTVLDMRSMDFKSNSAVAWSNKSD

FACANAFNNSIIPEDTFFPSPESSCDVKLVEKSFETDTNLNFQNLSVIGF

RILLLKVAGFNLLMTLRLWSS

SEQ ID NO. 4 shows the TCR beta chain sequence of clone CTL 1A.1/506

MGTRLFFYVALCLLWTGHMDAGITQSPRHKVTETGTPVTLRCHQTENHRY

MYWYRQDPGHGLRLIHYSYGVKDTDKGEVSDGYSVSRSKTEDFLLTLESA

TSSQTSVYFCAISEKLAGAYEQYFGPGTRLTVTEDLKNVFPPEVAVFEPS

EAEISHTQKATLVCLATGFYPDHVELSWWVNGKEVHSGVSTDPQPLKEQP

ALNDSRYCLSSRLRVSATFWQNPRNHFRCQVQFYGLSENDEWTQDRAKPV

TQIVSAEAWGRADCGFTSESYQQGVLSATILYEILLGKATLYAVLVSALV

LMAMVKRKDSRG

SEQ ID NO. 5 shows the TCR alpha chain sequence of clone CTL 2C/417

MASAPISMLAMLFTLSGLRAQSVAQPEDQVNVAEGNPLTVKCTYSVSGNP

YLFWYVQYPNRGLQFLLKYITGDNLVKGSYGFEAEFNKSQTSFHLKKPSA

LVSDSALYFCAVRDMIEGGGNKLTFGTGTQLKVELNIQNPDPAVYQLRDS

KSSDKSVCLFTDFDSQTNVSQSKDSDVYITDKTVLDMRSMDFKSNSAVAW

SNKSDFACANAFNNSIIPEDTFFPSPESSCDVKLVEKSFETDTNLNFQNL

SVIGFRILLLKVAGFNLLMTLRLWSS

SEQ ID NO. 6 shows the TCR beta chain sequence of clone CTL 2C/417

MGIRLLCRVAFCFLAVGLVDVKVTQSSRYLVKRTGEKVFLECVQDMDHEN

MFWYRQDPGLGLRLIYFSYDVKMKEKGDIPEGYSVSREKKERFSLILESA

STNQTSMYLCASSRQGAVGQPQHFGDGTRLSILEDLNKVFPPEVAVFEPS

EAEISHTQKATLVCLATGFFPDHVELSWWVNGKEVHSGVSTDPQPLKEQP

ALNDSRYCLSSRLRVSATFWQNPRNHFRCQVQFYGLSENDEWTQDRAKPV

TQIVSAEAWGRADCGFTSVSYQQGVLSATILYEILLGKATLYAVLVSALV

LMAMVKRKDF

SEQ ID NO. 7 shows the TCR alpha chain sequence of clone CTL 1A3/46

MSLSSLLKVVTASLWLGPGIAQKITQTQPGMFVQEKEAVTLDCTYDTSDP

SYGLFWYKQPSSGEMIFLIYQGSYDQQNATEGRYSLNFQKARKSANLVIS

ASQLGDSAMYFCAMRPHFGNEKLTFGTGTRLTIIPNIQNPDPAVYQLRDS

KSSDKSVCLFTDFDSQTNVSQSKDSDVYITDKTVLDMRSMDFKSNSAVAW

SNKSDFACANAFNNSIIPEDTFFPSPESSCDVKLVEKSFETDTNLNFQNL

SVIGFRILLLKVAGFNLLMTLRLWSS

SEQ ID NO. 8 shows the TCR beta chain sequence of clone CTL 1A3/46

MGTRLFFYVALCLLWTGHMDAGITQSPRHKVTETGTPVTLRCHQTENHRY

MYWYRQDPGHGLRLIHYSYGVKDTDKGEVSDGYSVSRSKTEDFLLTLESA

TSSQTSVYFCAISEKLAGAYEQYFGPGTRLTVTEDLKNVFPPEVAVFEPS

EAEISHTQKATLVCLATGFYPDHVELSWWVNGKEVHSGVSTDPQPLKEQP

ALNDSRYCLSSRLRVSATFWQNPRNHFRCQVQFYGLSENDEWTQDRAKPV

TQIVSAEAWGRADCGFTSESYQQGVLSATILYEILLGKATLYAVLVSALV

LMAMVKRKDSRG*

SEQ ID NOs 9 to 26 show the CDR sequences of the TCR of the invention.

EXAMPLES

Example 1

Generation of Melanoma-Reactive CD8 Positive T Cells

Out of the melanoma patient MA-MEL-86 four different permanent tumor cell lines (MA-MEL-86A, -86B, -86C, -86F) were established from separate lymph node metastases. Both MA-MEL-86B and MA-MEL-86F did not express HLA I on their cellular surface due to a biallelic mutation in the β2-microglobulin gene. The tumor cell line MA-MEL-86C lost one HLA haplotype. In contrast thereto, the MA-MEL-86A line expressed all HLA I alleles, but showed as the only one out of the four tumor cell lines no expression of melanosomal differentiation antigens (FIG. 1).

Tumor-reactive CD8 positive T cells were generated in so called mixed lymphocyte-tumor cell culture (MLTC) by weekly stimulation of lymphocytes taken from peripheral blood mononuclear cells, PBMCs, with autologous tumor cell lines MA-MEL-86A or MA-MEL-86C. Surprisingly, the inventors recognized that MLTC-responder lymphocytes in varying recognition patterns still recognized the HLA I negative variants MA-MEL-86B (FIG. 2) and MA-MEL-86F. This was confirmed with clonal T cells (CTL) from these MLTCs. MLTCs and CTL clones were used for the identification of their target molecules.

Example 2

Identification of CSF2RA

A cDNA library of the melanoma cell line MEL-86A constructed in the eukaryotic expression vector pcDNA3.1 was screened with responder lymphocytes of MLTC 1A.1. In a first step, cDNA pools consisting of 100 cDNA clones were co-transfected with HLA I alleles of the patient into 293T-cells. The transfectants were tested for recognition by the T cells. One of the pools was found to be responsive. Subsequently, a step-by-step cDNA cloning was performed. In this way CSF2RA was identified as a target of the MLTC 1A.1 (FIG. 3). Then T cell clones were isolated which were able to detect the HLA I negative melanoma cell variants and which were directed against CSF2RA. In particular when looking at the cross-reactivity of T cells against CSF2RA, one recognizes the particularity of the antigen. The CSF2RA-reactive T cells were able to detect 60% of the available melanoma cells lines, but also tumor cell lines of pancreas, colon, lung, ovarian, gallbladder origin as well as myeloid leukemias (Table 2).

TABLE 2

Allogeneic tumor lines recognized by
the CSF2RA-reactive CTL 1A.1/506.

| Analyzed tumor lines | recognition/n tested |
|---|---|
| Melanomas | 12/20 |
| Pankreas carcinomas (PC) | 2/2 |
| Kidney carcinomas (RCC) | 0/5 |
| Acute myeloid Leukemias (AML) | 5/13 |
| Chronic myelogenous Leukemias (CML) | 0/11 |
| Colorectal carcinomas (CRC) | 1/6 |
| Lung carcinomas | 1/4 |
| Breast carcinoma | 0/1 |
| Ovarian carcinoma | 1/1 |
| Gallbladder carcinoma | 1/1 |
| Glioblastoma | 0/11 |

On the other hand, all tested normal cell lines, amongst others melanocytes, granulocytes and monocytes, derived from peripheral blood, were not recognized by the CSF2RA-reactive T cells (see FIG. 4). The purity of the cell preparations were tested in advance via flow cytometry. Furthermore, subsequent to a transfection with CSF2RA, cell lines from different species could be detected by the CSF2RA-reactive T cells (see FIG. 5). A co-transfection with HLA I was not necessary.

Using flow cytometry the inventors furthermore showed that all CSF2RA-reactive T-cells were TCRαβ positive, CD3 positive and CD8 positive, and expressed the T cell receptor beta chain Vβ12 (TRBV10-3). The reactivity of these T cells could only be inhibited by antibodies against CD3 or CSF2RA, but not with antibodies against HLA I or II (see FIG. 6). cDNAs of the alpha and the beta chain of the TCR of the HLA-independent CSF2RA-reactive T-cell clone 1A.1/506 were cloned and sequenced (see FIG. 7, SEQ ID No. 3 and 4).

Example 3

Identification of TRP-2

In panel test 40 cDNA clones which encode known melanoma-associated antigens, were transfected into 293T cells. The transfectants were subsequently tested for recognition by responder lymphocytes of MLTCs 1C and 2C. It was found that both MLTCs and CTL clones derived thereof could recognize the HLA I negative tumor cell lines MA-MEL-86B and -86F and targeted the melanosomal differentiation antigen TRP-2. They cross-reacted with any of the TRP-2-expressing melanoma cell lines available in the laboratory as well as with normal melanocytes, and—after transfection with TRP-2—also with non-melanocytic cells of mouse, hamster and monkey origin (see FIG. 8). A co-transfection of HLA I molecules was not necessary. The HLA-independent TRP-2 reactive T cells recognized also murine melanoma cells and murine TRP-2 after transfection.

Using flow cytometry the inventors furthermore showed that all TRP-2-reactive T cells were TCRαβ positive, CD3 positive and CD8 positive, and expressed the T-cell receptor beta chain Vβ3 (TRBV28). The reactivity of these T cells could only be inhibited by antibodies against CD3, but not by antibodies against HLA I or II.

The direct recognition of TRP-2 by CD8 positive T cells would require the cell surface expression of the antigen. Indeed the inventors could show cell surface expression with a TRP-2 reactive antibody (see FIG. 9). For a clear-cut evidence of TRP-2 on the surface of human melanoma cells, the inventors used recombinant DNA technology to modify TRP-2 with a 13 amino acid-long alpha-bungarotoxin recognition site. This site is able to bind the neurotoxin alpha-BTX with high affinity and specificity. Using alpha-BTX coupled to a fluorochrome, visualization of the TRP-2 fusion protein on the cell surface of transfectants became possible (see FIG. 10).

This result was further supported by the finding that a deletion of the transmembrane domain (TMD) of TRP-2 resulted in a loss of the recognition by the T cells, which could be reversed by the substitution with an unrelated TMD of HLA-A*24:01 (see FIG. 11).

cDNAs of the alpha and the beta chain of the TCR of the HLA-independent TRP-2-reactive T-cell clone 2C/417 were cloned and their function was tested via transfer into CD8 positive T cells of PBMCs of a healthy donor (SEQ ID No. 5 and 6; FIG. 12).

Example 4

Cloning, Ectopic Expression and Functional Analysis of a Second CSF2RA-specific a/b T Cell Receptor The a- and b T cell receptor chain- (TCR-) cDNAs were isolated from the CSF2RA-specific CTL 1A.3/46 and cloned as a bicistronic construct into a retroviral vector (FIG. 13A). Subsequently, the human constant domains were replaced by murine TCR-constant domains ("chimerized" or "murinized") to minimize pairing of transduced with endogenous TCR-chains after ectopic expression in human T cells.

Cell surface expression of the CSF2RA-specific TCR in human T cells transduced with the native (left) and the chimerized (right) constructs is shown in FIG. 13B. The percentage of TCR-Vb12-positive T cells in untransduced PBMCs in this sample was <3% (not shown).

In a response analysis of the CSF2RA-reactive CTL 1A.3/44 in comparison to CSF2RA-TCR-transduced allogeneic T cells CSF2RA-negative target cells (MA-MEL-86F and 293T) were not recognized while MA-MEL-86B cells expressing CSF2RA endogenously and 293T cells transfected with the antigen were recognized (FIG. 13C). T cells transduced with the chimerized TCR showed a response comparable to that of the CSF2RA-reactive CTL 1A.3/44 and significantly higher reactivity than T cells transduced with the "native" TCR construct.

The invention claimed is:
1. A T cell receptor (TCR), or a binding fragment thereof, the TCR comprising:
   i) SEQ ID NO: 14,
   ii) SEQ ID NOs: 12, 13, and 14,
   wherein the TCR is (i) a chimeric TCR, (ii) a γδ TCR, (iii) a binding fragment of a TCR, or (iv) a single chain TCR (scTCR).
2. A pharmaceutical composition, comprising
   a TCR, or a binding fragment thereof, according to claim 1; and
   a pharmaceutically acceptable carrier or diluent.

* * * * *

SEQUENCE LISTING

```
<160> NUMBER OF SEQ ID NOS: 26

<210> SEQ ID NO 1
<211> LENGTH: 400
<212> TYPE: PRT
<213> ORGANISM: Homo sapiens

<400> SEQUENCE: 1

Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
    50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Glu Arg Phe Asn Pro Pro Ser Asn Val
    210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
        275                 280                 285

Arg Ala Lys His Ser Val Lys Ile Arg Ala Ala Asp Val Arg Ile Leu
    290                 295                 300

Asn Trp Ser Ser Trp Ser Glu Ala Ile Glu Phe Gly Ser Asp Asp Gly
305                 310                 315                 320
```

```
Asn Leu Gly Ser Val Tyr Ile Tyr Val Leu Ile Val Gly Thr Leu
                325                 330                 335

Val Cys Gly Ile Val Leu Gly Phe Leu Phe Lys Arg Phe Leu Arg Ile
            340                 345                 350

Gln Arg Leu Phe Pro Pro Val Pro Gln Ile Lys Asp Lys Leu Asn Asp
        355                 360                 365

Asn His Glu Val Glu Asp Glu Ile Ile Trp Glu Gln Phe Thr Pro Glu
    370                 375                 380

Glu Gly Lys Gly Tyr Arg Glu Glu Val Leu Thr Val Lys Glu Ile Thr
385                 390                 395                 400

<210> SEQ ID NO 2
<211> LENGTH: 519
<212> TYPE: PRT
<213> ORGANISM: Homo sapiens

<400> SEQUENCE: 2

Met Ser Pro Leu Trp Trp Gly Phe Leu Leu Ser Cys Leu Gly Cys Lys
1               5                   10                  15

Ile Leu Pro Gly Ala Gln Gly Gln Phe Pro Arg Val Cys Met Thr Val
            20                  25                  30

Asp Ser Leu Val Asn Lys Glu Cys Cys Pro Arg Leu Gly Ala Glu Ser
        35                  40                  45

Ala Asn Val Cys Gly Ser Gln Gln Gly Arg Gly Gln Cys Thr Glu Val
    50                  55                  60

Arg Ala Asp Thr Arg Pro Trp Ser Gly Pro Tyr Ile Leu Arg Asn Gln
65                  70                  75                  80

Asp Asp Arg Glu Leu Trp Pro Arg Lys Phe Phe His Arg Thr Cys Lys
                85                  90                  95

Cys Thr Gly Asn Phe Ala Gly Tyr Asn Cys Gly Asp Cys Lys Phe Gly
            100                 105                 110

Trp Thr Gly Pro Asn Cys Glu Arg Lys Lys Pro Pro Val Ile Arg Gln
        115                 120                 125

Asn Ile His Ser Leu Ser Pro Gln Glu Arg Glu Gln Phe Leu Gly Ala
    130                 135                 140

Leu Asp Leu Ala Lys Lys Arg Val His Pro Asp Tyr Val Ile Thr Thr
145                 150                 155                 160

Gln His Trp Leu Gly Leu Leu Gly Pro Asn Gly Thr Gln Pro Gln Phe
                165                 170                 175

Ala Asn Cys Ser Val Tyr Asp Phe Phe Val Trp Leu His Tyr Tyr Ser
            180                 185                 190

Val Arg Asp Thr Leu Leu Gly Pro Gly Arg Pro Tyr Arg Ala Ile Asp
        195                 200                 205

Phe Ser His Gln Gly Pro Ala Phe Val Thr Trp His Arg Tyr His Leu
    210                 215                 220

Leu Cys Leu Glu Arg Asp Leu Gln Arg Leu Ile Gly Asn Glu Ser Phe
225                 230                 235                 240

Ala Leu Pro Tyr Trp Asn Phe Ala Thr Gly Arg Asn Glu Cys Asp Val
                245                 250                 255

Cys Thr Asp Gln Leu Phe Gly Ala Ala Arg Pro Asp Asp Pro Thr Leu
            260                 265                 270

Ile Ser Arg Asn Ser Arg Phe Ser Ser Trp Glu Thr Val Cys Asp Ser
        275                 280                 285

Leu Asp Asp Tyr Asn His Leu Val Thr Leu Cys Asn Gly Thr Tyr Glu
    290                 295                 300
```

-continued

```
Gly Leu Leu Arg Arg Asn Gln Met Gly Arg Asn Ser Met Lys Leu Pro
305                 310                 315                 320

Thr Leu Lys Asp Ile Arg Asp Cys Leu Ser Leu Gln Lys Phe Asp Asn
            325                 330                 335

Pro Pro Phe Phe Gln Asn Ser Thr Phe Ser Phe Arg Asn Ala Leu Glu
        340                 345                 350

Gly Phe Asp Lys Ala Asp Gly Thr Leu Asp Ser Gln Val Met Ser Leu
    355                 360                 365

His Asn Leu Val His Ser Phe Leu Asn Gly Thr Asn Ala Leu Pro His
370                 375                 380

Ser Ala Ala Asn Asp Pro Ile Phe Val Val Leu His Ser Phe Thr Asp
385                 390                 395                 400

Ala Ile Phe Asp Glu Trp Met Lys Arg Phe Asn Pro Pro Ala Asp Ala
            405                 410                 415

Trp Pro Gln Glu Leu Ala Pro Ile Gly His Asn Arg Met Tyr Asn Met
        420                 425                 430

Val Pro Phe Phe Pro Val Thr Asn Glu Glu Leu Phe Leu Thr Ser
    435                 440                 445

Asp Gln Leu Gly Tyr Ser Tyr Ala Ile Asp Leu Pro Val Ser Val Glu
450                 455                 460

Glu Thr Pro Gly Trp Pro Thr Thr Leu Leu Val Val Met Gly Thr Leu
465                 470                 475                 480

Val Ala Leu Val Gly Leu Phe Val Leu Leu Ala Phe Leu Gln Tyr Arg
                485                 490                 495

Arg Leu Arg Lys Gly Tyr Thr Pro Leu Met Glu Thr His Leu Ser Ser
        500                 505                 510

Lys Arg Tyr Thr Glu Glu Ala
        515

<210> SEQ ID NO 3
<211> LENGTH: 271
<212> TYPE: PRT
<213> ORGANISM: Homo sapiens

<400> SEQUENCE: 3

Met Glu Thr Leu Leu Gly Pro Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Ser Gly Asp Ser Ala Thr Tyr Leu Cys Ala Val Gly
            100                 105                 110

Gly Asn Asp Tyr Lys Leu Ser Phe Gly Ala Gly Thr Thr Val Thr Val
        115                 120                 125

Arg Ala Asn Ile Gln Asn Ser Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160
```

```
Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
            245                 250                 255

Val Ala Gly Phe Asn Leu Leu Met Thr Leu Arg Leu Trp Ser Ser
        260                 265                 270
```

<210> SEQ ID NO 4
<211> LENGTH: 312
<212> TYPE: PRT
<213> ORGANISM: Homo sapiens

<400> SEQUENCE: 4

```
Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30

Glu Thr Gly Thr Pro Val Thr Leu Arg Cys His Gln Thr Glu Asn His
        35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Glu Lys Leu Ala Gly Ala Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270
```

Gln Gly Val Leu Ser Ala Thr Ile Leu Tyr Glu Ile Leu Gly Lys
             275                 280                 285

Ala Thr Leu Tyr Ala Val Leu Val Ser Ala Leu Val Leu Met Ala Met
290                 295                 300

Val Lys Arg Lys Asp Ser Arg Gly
305                 310

<210> SEQ ID NO 5
<211> LENGTH: 276
<212> TYPE: PRT
<213> ORGANISM: Homo sapiens

<400> SEQUENCE: 5

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
             20                  25                  30

Ala Glu Gly Asn Pro Leu Thr Val Lys Cys Thr Tyr Ser Val Ser Gly
         35                  40                  45

Asn Pro Tyr Leu Phe Trp Tyr Val Gln Tyr Pro Asn Arg Gly Leu Gln
     50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                 85                  90                  95

Lys Pro Ser Ala Leu Val Ser Asp Ser Ala Leu Tyr Phe Cys Ala Val
            100                 105                 110

Arg Asp Met Ile Glu Gly Gly Asn Lys Leu Thr Phe Gly Thr Gly
        115                 120                 125

Thr Gln Leu Lys Val Glu Leu Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 6
<211> LENGTH: 310
<212> TYPE: PRT
<213> ORGANISM: Homo sapiens

```
<400> SEQUENCE: 6

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Arg Gln Gly Ala Val Gly Gln Pro Gln His Phe Gly Asp Gly Thr
        115                 120                 125

Arg Leu Ser Ile Leu Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 7
<211> LENGTH: 276
<212> TYPE: PRT
<213> ORGANISM: Homo sapiens

<400> SEQUENCE: 7

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45
```

-continued

```
Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
 65                  70                  75                  80

Glu Gly Arg Tyr Ser Leu Asn Phe Gln Lys Ala Arg Lys Ser Ala Asn
                 85                  90                  95

Leu Val Ile Ser Ala Ser Gln Leu Gly Asp Ser Ala Met Tyr Phe Cys
            100                 105                 110

Ala Met Arg Pro His Phe Gly Asn Glu Lys Leu Thr Phe Gly Thr Gly
            115                 120                 125

Thr Arg Leu Thr Ile Ile Pro Asn Ile Gln Asn Pro Asp Pro Ala Val
130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
            275

<210> SEQ ID NO 8
<211> LENGTH: 312
<212> TYPE: PRT
<213> ORGANISM: Homo sapiens

<400> SEQUENCE: 8

Met Gly Thr Arg Leu Phe Phe Tyr Val Ala Leu Cys Leu Leu Trp Thr
 1                   5                  10                  15

Gly His Met Asp Ala Gly Ile Thr Gln Ser Pro Arg His Lys Val Thr
                 20                  25                  30

Glu Thr Gly Thr Pro Val Thr Leu Arg Cys His Gln Thr Glu Asn His
             35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
 65                  70                  75                  80

Asp Gly Tyr Ser Val Ser Arg Ser Lys Thr Glu Asp Phe Leu Leu Thr
                 85                  90                  95

Leu Glu Ser Ala Thr Ser Ser Gln Thr Ser Val Tyr Phe Cys Ala Ile
            100                 105                 110

Ser Glu Lys Leu Ala Gly Ala Tyr Glu Gln Tyr Phe Gly Pro Gly Thr
            115                 120                 125

Arg Leu Thr Val Thr Glu Asp Leu Lys Asn Val Phe Pro Pro Glu Val
130                 135                 140
```

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
            165                 170                 175

Ser Trp Trp Val Asn Gly Lys Glu Val His Ser Gly Val Ser Thr Asp
        180                 185                 190

Pro Gln Pro Leu Lys Glu Gln Pro Ala Leu Asn Asp Ser Arg Tyr Cys
    195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
            245                 250                 255

Glu Ala Trp Gly Arg Ala Asp Cys Gly Phe Thr Ser Glu Ser Tyr Gln
        260                 265                 270

Gln Gly Val Leu Ser Ala Thr Ile Leu Tyr Glu Ile Leu Leu Gly Lys
    275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 9
<211> LENGTH: 6
<212> TYPE: PRT
<213> ORGANISM: Homo sapiens

<400> SEQUENCE: 9

Asp Ser Ala Ile Tyr Asn
1               5

<210> SEQ ID NO 10
<211> LENGTH: 7
<212> TYPE: PRT
<213> ORGANISM: Homo sapiens

<400> SEQUENCE: 10

Ile Gln Ser Ser Gln Arg Glu
1               5

<210> SEQ ID NO 11
<211> LENGTH: 11
<212> TYPE: PRT
<213> ORGANISM: Homo sapiens

<400> SEQUENCE: 11

Cys Ala Val Gly Gly Asn Asp Tyr Lys Leu Ser
1               5                   10

<210> SEQ ID NO 12
<211> LENGTH: 5
<212> TYPE: PRT
<213> ORGANISM: Homo sapiens

<400> SEQUENCE: 12

Glu Asn His Arg Tyr
1               5

```
<210> SEQ ID NO 13
<211> LENGTH: 6
<212> TYPE: PRT
<213> ORGANISM: Homo sapiens

<400> SEQUENCE: 13

Ser Tyr Gly Val Lys Asp
1               5

<210> SEQ ID NO 14
<211> LENGTH: 14
<212> TYPE: PRT
<213> ORGANISM: Homo sapiens

<400> SEQUENCE: 14

Cys Ala Ile Ser Glu Lys Leu Ala Gly Ala Tyr Glu Gln Tyr
1               5                   10

<210> SEQ ID NO 15
<211> LENGTH: 6
<212> TYPE: PRT
<213> ORGANISM: Homo sapiens

<400> SEQUENCE: 15

Val Ser Gly Asn Pro Tyr
1               5

<210> SEQ ID NO 16
<211> LENGTH: 8
<212> TYPE: PRT
<213> ORGANISM: Homo sapiens

<400> SEQUENCE: 16

Tyr Ile Thr Gly Asp Asn Leu Val
1               5

<210> SEQ ID NO 17
<211> LENGTH: 15
<212> TYPE: PRT
<213> ORGANISM: Homo sapiens

<400> SEQUENCE: 17

Cys Ala Val Arg Asp Met Ile Glu Gly Gly Asn Lys Leu Thr
1               5                   10                  15

<210> SEQ ID NO 18
<211> LENGTH: 5
<212> TYPE: PRT
<213> ORGANISM: Homo sapiens

<400> SEQUENCE: 18

Met Asp His Glu Asn
1               5

<210> SEQ ID NO 19
<211> LENGTH: 6
<212> TYPE: PRT
<213> ORGANISM: Homo sapiens

<400> SEQUENCE: 19

Ser Tyr Asp Val Lys Met
1               5
```

-continued

```
<210> SEQ ID NO 20
<211> LENGTH: 14
<212> TYPE: PRT
<213> ORGANISM: Homo sapiens

<400> SEQUENCE: 20

Cys Ala Ser Ser Arg Gln Gly Ala Val Gly Gln Pro Gln His
1               5                   10

<210> SEQ ID NO 21
<211> LENGTH: 7
<212> TYPE: PRT
<213> ORGANISM: Homo sapiens

<400> SEQUENCE: 21

Thr Ser Asp Pro Ser Tyr Gly
1               5

<210> SEQ ID NO 22
<211> LENGTH: 8
<212> TYPE: PRT
<213> ORGANISM: Homo sapiens

<400> SEQUENCE: 22

Gln Gly Ser Tyr Asp Gln Gln Asn
1               5

<210> SEQ ID NO 23
<211> LENGTH: 13
<212> TYPE: PRT
<213> ORGANISM: Homo sapiens

<400> SEQUENCE: 23

Cys Ala Met Arg Pro His Phe Gly Asn Glu Lys Leu Thr
1               5                   10

<210> SEQ ID NO 24
<211> LENGTH: 5
<212> TYPE: PRT
<213> ORGANISM: Homo sapiens

<400> SEQUENCE: 24

Glu Asn His Arg Tyr
1               5

<210> SEQ ID NO 25
<211> LENGTH: 6
<212> TYPE: PRT
<213> ORGANISM: Homo sapiens

<400> SEQUENCE: 25

Ser Tyr Gly Val Lys Asp
1               5

<210> SEQ ID NO 26
<211> LENGTH: 14
<212> TYPE: PRT
<213> ORGANISM: Homo sapiens

<400> SEQUENCE: 26

Cys Ala Ile Ser Glu Lys Leu Ala Gly Ala Tyr Glu Gln Tyr
1               5                   10
```